US009826734B2

(12) United States Patent
Baur et al.

(10) Patent No.: US 9,826,734 B2
(45) Date of Patent: Nov. 28, 2017

(54) ETHERIFIED LACTATE ESTERS, METHOD FOR THE PRODUCTION THEREOF AND USE THEREOF FOR ENHANCING THE EFFECT OF PLANT PROTECTING AGENTS

(75) Inventors: Peter Baur, Schondorf (DE); Klaus Lorenz, Dormagen (DE); Jorg Hofmann, Krefeld (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/234,473

(22) PCT Filed: Jul. 23, 2012

(86) PCT No.: PCT/EP2012/064421
§ 371 (c)(1),
(2), (4) Date: Jun. 24, 2014

(87) PCT Pub. No.: WO2013/014126
PCT Pub. Date: Jan. 31, 2013

(65) Prior Publication Data
US 2014/0316157 A1 Oct. 23, 2014

Related U.S. Application Data

(60) Provisional application No. 61/511,601, filed on Jul. 26, 2011.

(30) Foreign Application Priority Data

Jul. 26, 2011 (EP) .................................... 11175341

(51) Int. Cl.
| | | |
|---|---|---|
| *A01N 25/22* | (2006.01) | |
| *C07C 69/708* | (2006.01) | |
| *C07C 67/31* | (2006.01) | |
| *A01N 25/30* | (2006.01) | |
| *A01N 37/36* | (2006.01) | |

(52) U.S. Cl.
CPC .............. *A01N 25/22* (2013.01); *A01N 25/30* (2013.01); *A01N 37/36* (2013.01); *C07C 67/31* (2013.01); *C07C 69/708* (2013.01)

(58) Field of Classification Search
CPC ........ A01N 25/22; C07C 69/708; C07C 67/31
See application file for complete search history.

(56) References Cited

U.S. PATENT DOCUMENTS

| | | |
|---|---|---|
| 3,404,109 A | 10/1968 | Milgrom |
| 3,829,505 A | 8/1974 | Johnston |
| 3,941,849 A | 3/1976 | Herold |
| 5,158,922 A | 10/1992 | Hinney et al. |
| 5,470,813 A | 11/1995 | Le-Khac |
| 6,835,687 B2 | 12/2004 | Hofmann et al. |
| 7,008,900 B1 | 3/2006 | Hofmann et al. |
| 7,407,667 B2 | 8/2008 | Zerrer et al. |
| 7,459,477 B2 | 12/2008 | Furuya et al. |
| 7,662,972 B2 | 2/2010 | Mita et al. |
| 7,872,036 B2 | 1/2011 | Toriyabe et al. |
| 7,897,543 B2 | 3/2011 | Bretschneider et al. |
| 8,084,452 B2 | 12/2011 | Jeschke et al. |
| 8,106,212 B2 | 1/2012 | Jeschke et al. |
| 8,138,350 B2 | 3/2012 | Jeschke et al. |
| 8,202,890 B2 | 6/2012 | Goto et al. |
| 8,324,390 B2 | 12/2012 | Fischer et al. |
| 8,470,856 B2 | 6/2013 | Koyanagi et al. |
| 8,546,577 B2 | 10/2013 | Jeschke et al. |
| 8,697,867 B2 | 4/2014 | Hamamoto et al. |
| 8,759,255 B2 | 6/2014 | Wacker et al. |
| 8,809,547 B2 | 8/2014 | Bretschneider et al. |
| 9,000,189 B2 | 4/2015 | Bretschneider et al. |
| 2005/0037926 A1 | 2/2005 | Zerrer et al. |
| 2006/0105002 A1* | 5/2006 | Selifonov ............. C07C 69/708 424/401 |
| 2009/0111847 A1 | 4/2009 | Li et al. |
| 2014/0128265 A1 | 5/2014 | Wacker |
| 2014/0141977 A1 | 5/2014 | Wacker et al. |
| 2014/0316157 A1 | 10/2014 | Baur et al. |
| 2015/0282478 A1 | 10/2015 | Baur et al. |
| 2015/0320037 A1 | 11/2015 | Wacker et al. |
| 2017/0042142 A1 | 2/2017 | Baur et al. |

FOREIGN PATENT DOCUMENTS

| | | |
|---|---|---|
| DE | 10 2007 018 983 A1 | 10/2008 |
| EP | 0539588 | 5/1993 |
| EP | 0700949 | 3/1996 |
| EP | 0743093 | 11/1996 |
| EP | 0761708 | 3/1997 |
| EP | 1 702941 A1 | 9/2006 |
| JP | 06-122655 A | 5/1994 |
| JP | 01-113391 A | 5/1999 |
| JP | 2008/110953 | 5/2008 |

(Continued)

OTHER PUBLICATIONS

International Search Report of PCT/EP2012/064421 dated Sep. 1, 2013.
International Preliminary Report of Patentability of PCT/EP2012/064421 dated Jan. 28, 2014.
"The Pesticide Manual" 14th Ed., British Crop Protection Council 2006.
"The Pesticide Manual", 15th edition, The British Crop Protection Council and the Royal Soc. of Chemistry, 2006.
Crop Life International and in Pesticide Specifications, Manual on development and use of FAO and WHO specifications for pesticides, FAO Plant Production and Protection Papers-173, prepared by the FAO/WHO Joint Meeting on Pesticide Specifications, 2004, ISBN: 9251048576.

(Continued)

*Primary Examiner* — Clinton Brooks
(74) *Attorney, Agent, or Firm* — Tod A. Waldrop

(57) ABSTRACT

The invention relates to etherified lactate esters of formula (I), in which R represents alkyl and RI an alkoxylated alkyl radical and to the use thereof for enhancing the effect of plant protecting agents.

5 Claims, No Drawings

(56) References Cited

FOREIGN PATENT DOCUMENTS

| | | |
|---|---|---|
| JP | 2010/018586 | 1/2010 |
| WO | WO 91/14366 | 10/1991 |
| WO | WO 96/22020 | 7/1996 |
| WO | WO 97/29146 | 8/1997 |
| WO | WO 97/40086 | 10/1997 |
| WO | WO 98/03571 | 1/1998 |
| WO | WO 98/16310 | 4/1998 |
| WO | WO 99/14258 | 3/1999 |
| WO | WO 00/18227 | 4/2000 |
| WO | WO 00/47649 | 8/2000 |
| WO | WO 01/80994 | 11/2001 |
| WO | WO 02/096882 | 12/2002 |
| WO | WO 03/075657 | 9/2003 |
| WO | WO 03/106457 | 12/2003 |
| WO | WO 2004/099160 | 11/2004 |
| WO | WO 2005/035486 | 4/2005 |
| WO | WO 2005/077934 | 8/2005 |
| WO | WO 2005/085216 | 9/2005 |
| WO | WO 2006/043635 | 4/2006 |
| WO | WO 2006/056433 | 6/2006 |
| WO | WO 2006/089633 | 8/2006 |
| WO | WO 2006/100288 | 9/2006 |
| WO | 2007028538 A2 | 3/2007 |
| WO | WO 2007/040280 | 4/2007 |
| WO | WO 2007/057407 | 5/2007 |
| WO | WO 2007/075459 | 7/2007 |
| WO | WO 2007/101369 | 9/2007 |
| WO | WO 2007/115643 | 10/2007 |
| WO | WO 2007/115644 | 10/2007 |
| WO | WO 2007/115646 | 10/2007 |
| WO | WO 2007/149134 | 12/2007 |
| WO | WO 2008/009360 | 1/2008 |
| WO | WO 2008/066153 | 5/2008 |
| WO | WO 2008/067911 | 6/2008 |
| WO | WO 2008/104503 | 9/2008 |
| WO | WO 2009/049851 | 4/2009 |
| WO | WO 2010/005692 | 1/2010 |
| WO | WO 2010/006713 | 1/2010 |
| WO | WO 2010/069502 | 6/2010 |
| WO | WO 2010/074747 | 7/2010 |
| WO | WO 2010/074751 | 7/2010 |

OTHER PUBLICATIONS

Baur et al., 1997, Pesticide Science 51, 131-152.
"Physical Chemistry of Surfaces", Fifth Edition. A. W. Adamson. John Wiley & Sons, Inc., 1990. pp. xxi + 777.
Berger PD & Berger CH, 1993. Effect of Surfactant Type and Order of Addition on Droplet Size and Dynamic Interfacial Properties. Pesticide formulations and application systems, 13th vol., Berger, PD, Debisetty, BN, Hall, FR, Eds., American Society for Testing and Materials.
Knowles, DA 1998, Chemistry and Technology of Agrochemical Formulations, Kluwer Academic Publishers, Dordrecht.
R E Gaskin ed. Proceeding of the 8th International Symposium on Adjuvants for Agrochemicals. Publisher: International Society for Agrochemical Adjuvants (ISAA), Columbus, Ohio, USA), 2007.
Cronfeld, P, Lader, K. Baur, P. (2001). Classification of Adjuvants and Adjuvant Blends by Effects on Cuticular Penetration, Pesticide Formulations and Application Systems: Twentieth Volume, ASTM STP 1400, A. K. Viets, R. S. Tann, J. C. Mueninghoff, Edsl, American Society for Testing and Materials, West Conshohocken, PA 2001.
CIPAC Method MT47, Dec. 2012.
Weed Research 26 (1986) 441-445.
English Abstract for JP 2008/110953, May 15, 2008.
English Abstract for JP 2010/018586, Jan. 28, 2010.

\* cited by examiner

ETHERIFIED LACTATE ESTERS, METHOD FOR THE PRODUCTION THEREOF AND USE THEREOF FOR ENHANCING THE EFFECT OF PLANT PROTECTING AGENTS

The invention relates to new etherified lactate esters, to processes for preparing them and to their use for improving the activity of active agrochemical ingredients in and on plants.

WO-A-1991/14366 describes lactate and lactate derivatives as active ingredients which regulate the growth of grapevines. The substances here are prepared directly in water without further additions, in a specified dose, and are used as a foliar spray solution at an early growth stage of the grapevines. The use of lactate derivatives for improving the activity of crop protection compositions at the level of the plants is neither disclosed nor suggested in this document, however.

WO-A-2000/18227 describes alkyl lactates in high concentrations as suspension agents for insoluble active agrochemical ingredients in nonaqueous suspension concentrates. The use of alkyl lactates for improving the activity at the level of the plants is neither disclosed nor suggested in this document. WO-A-2000/18227 also does not disclose etherified lactate esters.

WO-A-2003/075657 describes lactate esters in high concentrations as crystallization inhibitors and solvents for insoluble active agrochemical ingredients, more particularly azole fungicides. The use of lactate esters for improving the activity at the level of the plants is also neither disclosed nor suggested in this document. WO-A-2003/075657 also does not disclose etherified lactate esters.

WO-A-1996/22020 describes the use of aliphatic esters as penetrants. WO-A-1996/22020, however, does not disclose etherified lactate esters. WO-A-2007/028538 describes lactate esters with a free hydroxyl function for improving the efficacy of crop protection compositions. WO-A-2007/028538, however, does not disclose etherified lactate esters.

EP-B-1 702 941 describes a process for preparing poly(etherester) polyols that comprises in a first step reacting monocarboxylic or polycarboxylic esters containing one or more hydroxyl groups with alkylene oxides, with ring opening, in the presence of DMC catalysts (double metal cyanide complex catalysis) to give the corresponding monocarboxylic or polycarboxylic esters with one or more attached polyether chains, the alkylene oxide addition reaction being carried out optionally in the presence of a diol or polyol, and the products prepared in step a) being subsequently transesterified, in a second step, to give OH-functional poly(etherester)s ([0015]). Suitable starting components for preparing the monocarboxylic or polycarboxylic esters with attached polyether chains include the esters of lactate acid ([0016]). Specific esters of lactic acid are not specified. The etherified lactic esters of the invention are likewise not disclosed. The details of the process are described in ([0017])-([0029]). According to EP-B-1 702 941, the poly(etherester) polyols thus prepared are utilized as starting materials for producing polyurethane materials.

Not described to date has been an application of lactate esters etherified on the hydroxyl group (lactate ester alkoxylates) as improvers of the activity of active agrochemical ingredients in crop protection compositions. Crop protection compositions here refers to the application form of the active agrochemical ingredients, e.g., the spray mixture.

It has now surprisingly been found that the activity of crop protection compositions at the level of the plants is improved significantly by means of certain etherified lactate esters. Accordingly, the etherified lactate esters of the invention, as wetting agents, promote not only the persistence of the spray mixture of the crop protection compositions comprising the active agrochemical ingredients on the plant, particularly on the leaves (improved retention), but also the penetration into the plant of the active agrochemical ingredients contained within the crop protection compositions (improved penetration). This improvement in properties is achieved even with etherified lactate ester concentrations which correspond to those of typical wetting agents or penetrants.

The invention provides etherified lactate esters of the formula (I)

$$\underset{H_3C}{\overset{O}{\underset{\|}{\text{C}}}}\!\!-\!\!\overset{R}{\underset{O}{\text{C}}}\!\!-\!\!O\!\!-\!\!R^1 \quad (I)$$

wherein
R is unbranched or branched, saturated or unsaturated $C_1$-$C_{20}$ alkyl, and
$R^1$ is an alkoxylated alkyl radical of the formula -(-AO)$_m$—R', where
AO is an ethylene oxide radical, a propylene oxide radial, a butylene oxide radical, or mixtures of ethylene oxide and propylene oxide radicals or mixtures of ethylene oxide and butylene oxide radicals, and
m stands for numbers from 1 to 30,
R' is hydrogen or is a branched or unbranched, saturated, partly saturated or unsaturated $C_1$-$C_{20}$ alkyl radical.

The ethylene oxide radical, the propylene oxide radical, and the butylene oxide radical here are also referred to below simply as EO, PO, and BO, respectively.

The key structural chemical element that distinguishes the etherified lactate esters of the invention from the lactate esters from the prior art is therefore that the etherified lactate esters of the invention are alkoxylated.

The etherified lactate esters of the invention are given general definition by the formula (I). Preferred radical definitions for the formulae identified above and below are given in the following text:
R is preferably unbranched or branched, saturated or unsaturated $C_2$-$C_{18}$ alkyl
$R^1$ is preferably an alkoxylated alkyl radical of the formula -(-AO)$_m$—R', where
AO is an ethylene oxide radical, a propylene oxide radial, a butylene oxide radical, or mixtures of ethylene oxide and propylene oxide radicals or mixtures of ethylene oxide and butylene oxide radicals, and
m stands for numbers from 2 to 20,
R' is hydrogen or is a branched or unbranched, saturated, partly saturated or unsaturated $C_1$-$C_{15}$ alkyl radical.
R is more preferably hexyl, 1-ethylhexyl, 2-ethylhexyl, 3-ethylhexyl, 4-ethylhexyl, lauryl palmityl, stearyl (C18) or oleyl (C18, partly unsaturated).
$R^1$ is more preferably an alkoxylated alkyl radical of the formula -(-AO)$_m$—R', where
AO is an ethylene oxide radical, a propylene oxide radical, a butylene oxide radical, or mixtures of ethylene oxide and propylene oxide radicals, and
m stands for numbers from 2 to 15, R' is hydrogen or is a branched or unbranched, saturated, partly saturated or unsaturated $C_1$-$C_{10}$ alkyl radical.

Especially preferred are the following compounds for which R is hexyl, 1-ethylhexyl, 2-ethylhexyl, 3-ethylhexyl, 4-ethylhexyl, lauryl ($C_{12}$), palmityl ($C_{16}$) or oleyl ($C_{18}$), and $R^1$ is an alkoxylated alkyl radical of the formula -(-AO)$_m$—R', where R' is hydrogen or methyl, where m stands for numbers from 2 to 15, and AO has the definition given above.

Especially preferred are the following compounds:

etherified lauryl lactate, i.e., R is lauryl ($C_{12}$ alkyl), R1 is -(-AO)$_m$—R', where R' is hydrogen and -(-AO)$_m$ is selected from the group consisting of the following alkoxylate radicals: -(EO)$_5$—(PO)$_2$, -(EO)$_5$—(PO)$_5$, -(EO)$_8$—(PO)$_2$, -(EO)$_8$—(PO)$_5$.

Etherified 2-ethylhexyl lactate, i.e., R is 2-ethylhexyl (—$CH_2$—$CH(C_2H_5)$—$(CH_2)_3$—$CH_3$), R1 is -(-AO)$_m$—R', where R' is hydrogen and -(-AO)$_m$ is selected from the group consisting of the following alkoxylate radicals: -(EO)$_2$—(PO)$_2$, -(EO)$_2$—(PO)$_5$, -(EO)$_2$—(PO)$_{10}$, -(EO)$_2$, -(EO)$_5$, -(EO)$_{10}$, -(EO)$_{15}$.

The etherified lactate esters of the invention that are described here encompass all enantiomers. The etherified lactate esters of the invention are preferably in the (S)-form, although the (R)-form can likewise be usefully employed.

The etherified lactate esters of the invention may be prepared by the process described in EP-B-1 702 941. For that purpose the lactate esters of the formula (II) in which R has the definition given above and in which R2 is R', where R' has the definition indicated above

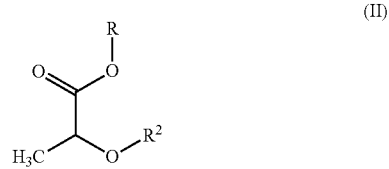

(II)

are prepared with alkylene oxides (EO, PO, BO or mixtures thereof) in the presence of DMC catalysts (double metal cyanide complex catalysis). The process conditions, the process profile, and the catalyst are known in principle from EP-B-1 702 941. In this regard, reference is made to EP-B-1 702 941, more particularly ([0015])-([0029]).

The lactate esters of the formula (II) that are used as a precursor are available commercially. The process in this case may be carried out as follows:

DMC catalysts suitable for the process of the invention are known in principle from the prior art (see, for example, U.S. Pat. No. 3,404,109, U.S. Pat. No. 3,829,505, U.S. Pat. No. 3,941,849, and U.S. Pat. No. 5,158,922). DMC catalysts, which are described in, for example, U.S. Pat. No. 5,470,813, EP-A 700949, EP-A 743093, EP-A 761708, WO 97/40086, WO 98/16310, WO 00/47649, and WO 01/80994, possess a very high activity in the polymerization of alkylene oxides, and allow the preparation of polyethers under optimum conditions for very low catalyst concentrations (100 ppm or less), meaning that it is no longer necessary to remove the catalyst from the finished product, in general. A typical example are the high-activity DMC catalysts described in EP-A 700949, which as well as a double metal cyanide compound (e.g., zinc hexacyanocobaltate(III)) and an organic complex ligand (e.g., tert-butanol), also comprise a polyether having a number-average molecular weight of greater than 500 g/mol.

The lactate esters in the formula (II) used in accordance with the invention as starter components may be included in the initial charge to the reactor or may be supplied continuously to the reactor during the reaction together with the alkylene oxides. In the case of the latter procedure, the initial charge to the reactor typically includes a small amount of an adduct of lactate ester of the formula (II) and alkylene oxide; this may also be the product that is to be prepared. A further possibility is to remove reaction product from the reactor continuously, in which case the DMC catalyst must also be metered in continuously, as well as alkylene oxide and the starter component. The process variants for the preparation of alkylene oxide adducts with DMC catalysis, with continuous metering of the starter components, are described in WO 97/29146 and WO 98/03571, for example.

The DMC-catalyzed reaction of the lactate esters of the formula (II) with the alkylene oxides takes place in general at temperatures from 20 to 200° C., preferably from 40 to 180° C., more preferably at temperatures from 50 to 150° C. The reaction can be carried out under total pressures of 0.0001 to 20 bar (absolute). The polyaddition may be carried out in bulk or in an inert organic solvent such as toluene and/or THF. The amount of solvent is typically 10 to 30 wt %, based on the amount of etherified lactate ester to be prepared.

The catalyst concentration is selected such that the polyaddition reaction is readily manageable under the prevailing reaction conditions. The catalyst concentration is in general 0.0005 wt % to 1 wt %, preferably 0.001 wt % to 0.1 wt %, more preferably 0.001 to 0.03 wt %, based on the amount of etherified lactate ester to be prepared. It is possible for the lactate esters of the formula (II) that are used in accordance with the invention as starter components to be admixed with small amounts (1-500 ppm, based on the amount of starter) of organic or inorganic acids, as described in WO 99/14258.

The etherified lactate esters prepared in this way may optionally be admixed with aging inhibitors such as antioxidants, for example.

The process for preparing the etherified lactate esters of the invention is likewise subject-matter of the process.

The invention also provides for use of the etherified lactate esters of the invention, of the formula (I)

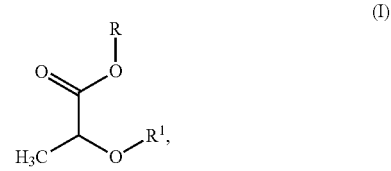

(I)

wherein the substituents R and R' have the definition given above, for improving activity of active agrochemical ingredients in and on plants. Particularly preferred in this context is the improvement in the penetration of active agrochemical ingredients into plants, and the improvement in the retention of active agrochemical ingredients on plants, more particularly on leaves.

The invention also provides the use of the etherified lactate esters of the invention as surfactant, as wetter and sticker, and as emulsifier.

Surprisingly it has been found that many of the etherified lactate esters of the invention exhibit excellent foaming behavior, meaning that they foam only to a small extent particularly in aqueous systems. The invention accordingly also provides the use of the etherified lactate esters of the invention for preventing or reducing foam formation in agrochemical formulations. When other penetrants are used, indeed, there is often intensified foam formation and hence the need additionally to employ defoamers.

The compounds of the formula (I) are used individually or in the form of mixtures. Where the description or the claims refer to etherified lactate esters, the reference explicitly is to individual compounds of the invention or to mixtures of two or more compounds of the invention.

The etherified lactate esters used in accordance with the invention may optionally take the form of mixtures of different possible isomeric forms, more particularly of stereoisomers, such as E- and Z-, threo- and erythro-, and also optical isomers. Employed with preference are L-lactate derivatives of the formula (I).

In the context of the inventive use in crop protection compositions, the amount of one or more compounds of the formula (I) may vary within wide limits according to active ingredient and type of formulation. The compounds of the formula (I) can be used in all customary agrochemical formulations, preferably in those which are liquid. The present invention also provides the use of the etherified lactate esters of the formula (I) for improving the activity at the level of the plant as a tank-mix additive, meaning that the etherified lactate esters are not added until directly before the application of a spray mixture produced from a concentrated formulation. In principle, however, the compounds may also be incorporated into solid formulations.

The inventive use of the etherified lactate esters of the formula (I) takes place, for example, in ready-to-apply crop protection compositions (spray mixtures), in which the amount of one or more etherified lactate esters in the formula (I) is 0.01 to 3 wt %,
more preferably 0.01 to 1 wt %,
very preferably 0.02 to 0.5 wt %,
especially preferably 0.03 to 0.3 wt %.

Where a crop protection composition comprises two or more etherified lactate esters, the quantity figure should be understood as the total content of all etherified lactate esters.

The radical definitions, value ranges and/or elucidations that are given above, whether those given generally or those given in ranges of preference, may also be combined arbitrarily with one another, hence including combinations between the respective ranges and preference ranges.

Since the mechanism of action of the etherified lactate esters as penetrants is fundamentally independent of the nature of the active agrochemical ingredient employed, their use is contemplated in crop protection compositions comprising at least one active ingredient whose biological activity may be enhanced by increased penetration into a crop plant or weed plant.

Since the mechanism of action of the etherified lactate esters as retention promoters is also fundamentally independent of the nature of the active agrochemical ingredient employed, their use is contemplated in crop protection compositions comprising at least one active ingredient whose biological activity may be enhanced by improved retention on the crop plant or weed plant.

Mention may preferably be made of fungicides, bactericides, insecticides, acaricides, nematicides, herbicides, plant growth regulators, plant nutrients, and repellents.

Examples of fungicides include:

(1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl) cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethyl-silyl)propoxy] phenyl}imidoformamide and O-[1-(4-methoxyphenoxy)-3, 3-dimethylbutan-2-yl]1H-imidazole-1-carbothioate.

(2) Respiration inhibitors (respiratory chain inhibitors), for example bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR, 9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2, 2-tetrafluoroethoxy)phenyl]-3-(trifluoromethyl)-1H-pyrazole-4-carboxamide, 3-(difluoromethyl)-1-methyl-N-[2-(1, 1,2,2-tetrafluoroethoxy)phenyl]-1H-pyrazole-4-carboxamide, 3-(difluoromethyl)-N-[4-fluoro-2-(1,1,2,3,3, 3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2-fluoro-4-{[4-(trifluoromethyl)pyridin-2-yl]oxy}phenyl)ethyl]quinazolin-4-amine, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl) ethanamide, (2E)-2-(methoxyimino)-N-methyl-2-{2-[(E)-({1-[3-(trifluoromethyl)phenyl]ethoxy}imino)methyl] phenyl}ethanamide, (2E)-2-{2-[({[(1E)-1-(3-{[(E)-1-fluoro-2-phenylethenyl]oxy}phenyl)ethylidene]amino}oxy) methyl]phenyl}-2-(methoxyimino)-N-methylethanamide, (2E)-2-{2-[({[(2E,3E)-4-(2,6-dichlorophenyl)but-3-en-2- ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methyl-4-(2,4,6-trifluorophenyl)pyridazine.

(5) Compounds with multisite activity, for example Bordeaux mixture, captafol, captan, chlorothalonil, copper preparations such as copper hydroxide, copper naphthenate, copper oxide, copper oxychloride, copper sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulfur and sulfur preparations, for example calcium polysulfide, thiram, tolylfluanid, zineb and ziram.

(6) Resistance inductors, for example acibenzolar-S-methyl, isotianil, probenazole and tiadinil.

(7) Amino acid and protein biosynthesis inhibitors, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) ATP production inhibitors, for example fentin acetate, fentin chloride, fentin hydroxide and silthiofam.

(9) Cell wall synthesis inhibitors, for example benthiavalicarb, dimethomorph, flumorph, iprovalicarb, mandipropamid, polyoxins, polyoxorim, validamycin A and valifenalate.

(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, for example carpropamid, diclocymet, fenoxanil, fthalide, pyroquilon, tricyclazole and 2,2,2-trifluoroethyl {3-methyl-1-[(4-methylbenzoyl)amino]butan-2-yl}carbamate.

(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Signal transduction inhibitors, for example chlozolinate, fenpiclonil, fludioxonil, iprodione, procymidone, quinoxyfen and vinclozolin.

(14) Decouplers, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulfate, diphenylamine, ecomat, fenpyrazamine, flumetover, fluoromide, flusulfamide, flutianil, fosetyl-aluminum, fosetyl-calcium, fosetyl-sodium, hexachlorobenzene, irumamycin, methasulfocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl)prop-2-en-1-one, pyrrolnitrin, tebufloquin, tecloftalam, tolnifanid, triazoxide, trichlamide, zarilamide, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2,6-dimethyl-1H,5H-[1,4]dithiino[2,3-c:5,6-c']dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-di hydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-fluoro-2-[(4-fluorobenzyl)oxy]pyrimidin-4-amine, 5-fluoro-2-[(4-methylbenzyl)oxy]pyrimidine-4-amin, 5-methyl-6-octyl[1,2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tertbutyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulfate (2:1) and tert-butyl {6-[({[(1-methyl-1H-tetrazol-5-yl)(phenyl)methylene]amino}oxy)methyl]pyridin-2-yl}carbamate.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methyl but-1-yn-1-yl)biphenyl-2-yl]-1,3-dimethyl-1H-pyrazole-4-carboxamide, 2-chloro-N-[4'-(3-methoxy-3-methyl but-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulfonyl)valinamide, 4-oxo-4-[(2-phenylethyl)amino]butanoic acid and but-3-yn-1-yl {6-[({[(Z)-(1-methyl-1H-tetrazol-5-yl)(phenyl)methylene]amino}oxy)methyl]pyridin-2-yl}carbamate.

All mixing components mentioned in classes (1) to (16) can, if they are capable on the basis of their functional groups, optionally form salts with suitable bases or acids.

Examples of bactericides include the following: bronopol, dichlorophen, nitrapyrin, nickel dimethyldithiocarbamate, kasugamycin, octhilinon, furancarboxylic acid, oxytetracycline, probenazole, streptomycin, tecloftalam, copper sulfate and other copper preparations.

Examples of insecticides, acaricides and nematicides include the following:

The active ingredients identified here by their common name are known and are described, for example, in the pesticide handbook ("The Pesticide Manual" 14th Ed., British Crop Protection Council 2006) or can be searched on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl (O-(methoxyaminothiophosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, such as, for example, cyclodiene organochlorines, for example chlordane and endosulfan; or phenylpyrazoles (fiproles), for example ethiprole and fipronil.

(3) Sodium channel modulators/voltage-dependent sodium channel blockers, such as, for example, pyrethroids, for example acrinathrin, allethrin (d-cis-trans, d-trans), bifenthrin, bioallethrin, bioallethrin-S-cyclopentenyl isomer, bioresmethrin, cycloprothrin, cyfluthrin (beta-), cyhalothrin (gamma-, lambda-), cypermethrin (alpha-, beta-, theta-, zeta-), cyphenothrin [(IR)-trans-isomers], deltamethrin, empenthrin [(EZ)-(IR)-isomers], esfenvalerate, etofenprox, fenpropathrin, fenvalerate, flucythrinate, flumethrin, fluvalinate (tau-), halfenprox, imiprothrin, kadethrin, permethrin, phenothrin [(IR)-trans-isomer], prallethrin, pyrethrins (pyrethrum), resmethrin, silafluofen, tefluthrin, tetramethrin, tetramethrin [(IR)-isomers], tralomethrin, and transfluthrin; or DDT; or methoxychlor.

(4) Nicotinergic acetylcholine receptor (nAChR) agonists, such as, for example, neonicotinoids, for example acetamiprid, clothianidin, dinotefuran, imidacloprid, nitenpyram, thiacloprid, and thiamethoxam; or nicotine.

(5) Nicotinergic acetylcholine receptor (nAChR) allosteric activators, such as, for example, spinosyns, for example spinetoram and spinosad.

(6) Chloride channel activators, such as, for example, avermectins/milbemycins, for example abamectin, emamectin benzoate, lepimectin and milbemectin.

(7) Juvenile hormone imitators, such as, for example juvenile hormone analogues, for example hydroprene, kinoprene, and methoprene; or fenoxycarb; or pyriproxyfen.

(8) Active ingredients with unknown or non-specific mechanisms of action, such as, for example, alkyl halides, for example methyl bromide and other alkyl halides; or chloropicrin; or sulfuryl fluoride; or borax; or tartar emetic.

(9) Selective antifeedants, for example pymetrozine; or flonicamid.

(10) Mite growth inhibitors, for example clofentezine, hexythiazox and diflovidazin; or etoxazole.

(11) Microbial disruptors of the insect gut membrane, such as, for example, *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: CryIAb, CryIAc, CryIFa, Cry2Ab, mCry3A, Cry3Ab, Cry3Bb, Cry34/35Ab1.

(12) Oxidative phosphorylation inhibitors, ATP disruptors, such as, for example, diafenthiuron; or organotin compounds, for example azocyclotin, cyhexatin and fenbutatin oxide; or propargite; or tetradifon.

(13) Oxidative phosphorylation decouplers acting by interrupting the H proton gradient, such as, for example, chlorfenapyr, DNOC and sulfluramid.

(14) Nicotinergic acetylcholine receptor antagonists, such as, for example, bensultap, cartap hydrochloride, thiocyclam, and thiosultap sodium.

(15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, such as, for example, buprofezin.

(17) Molting disruptors, dipteran, such as, for example, cyromazine.

(18) Ecdysone receptor agonists, such as, for example, chromafenozide, halofenozide, methoxyfenozide and tebufenozide.

(19) Octopaminergic agonists, such as, for example, amitraz.

(20) Complex-III electron transport inhibitors, such as, for example, hydramethylnon; or acequinocyl; or fluacrypyrim.

(21) Complex-I electron transport inhibitors, for example

METI acaricides, for example fenazaquin, fenpyroximate, pyrimidifen, pyridaben, tebufenpyrad and tolfenpyrad; or rotenone (Derris).

(22) Voltage-dependent sodium channel blockers, for example indoxacarb; or metaflumizone.

(23) Inhibitors of acetyl-CoA carboxylase, such as, for example, tetronic and tetramic acid derivatives, for example spirodiclofen, spiromesifen and spirotetramat.

(24) Complex-IV electron transport inhibitors, such as, for example, phosphines, for example aluminum phosphide, calcium phosphide, phosphine and zinc phosphide; or cyanide.

(25) Complex-II electron transport inhibitors, such as, for example, cyenopyrafen.

(28) Ryanodine receptor effectors, such as, for example, diamides, for example chlorantraniliprole and flubendiamide.

Further active ingredients with unknown mechanism of action, such as, for example, amidoflumet, azadirachtin, benclothiaz, benzoximate, bifenazate, bromopropylate, chinomethionat, cryolite, cyantraniliprole (cyazypyr), cyflumetofen, dicofol, diflovidazin, fluensulfone, flufenerim, flufiprole, fluopyram, fufenozide, imidaclothiz, iprodione, pyridalyl, pyrifluquinazon and iodomethane; and also products based on *Bacillus firmus* (1-1582, BioNeem, Votivo) and also the known active compounds below:

3-bromo-N-{2-bromo-4-chloro-6-[(1-cyclopropylethyl)carbamoyl]phenyl}-1-(3-chloropyridin-2-yl)-1H-pyrazole-5-carboxamide (known from WO 2005/077934), 4-{[(6-bromopyrid-3-yl)methyl](2-fluoroethyl)amino}furan-2 (5H)-one (known from WO 2007/115644), 4-{[(6-fluoropyrid-3-yl)methyl](2,2-difluoroethyl)amino}furan-2 (5H)-one (known from WO 2007/115644), 4-{[(2-chloro-1, 3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), 4-{[(6-chloropyrid-3-yl)methyl](2, 2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A 0 539 588), 4-{[(6-chloropyrid-3-yl)methyl](methyl)amino}furan-2 (5H)-one (known from EP-A 0 539 588), {[1-(6-chloropyridin-3-yl)ethyl](methyl)oxido-$\lambda^4$-sulfanylidene}cyanamide (known from WO 2007/149134) and its diastereomers {[(1R)-1-(6-chloropyridin-3-yl)ethyl](methyl)oxido-$\lambda^4$-sulfanylidene}cyanamide (A) and {[(1S)-1-(6-chloropyridin-3-yl)ethyl](methyl)oxido-$\lambda^4$-sulfanylidene}cyanamide (B) (likewise known from WO 2007/149134) and also sulfoxaflor (likewise known from WO 2007/149134) and its diastereomers [(R)-methyl(oxido){(1R)-1-[6-(trifluoromethyl)pyridin-3-yl]ethyl}-$\lambda^4$-sulfanylidene]cyanamide (A1) and [(S)-methyl (oxido){(1S)-1-[6-(trifluoromethyl)pyridin-3-yl]ethyl}-$\lambda^4$-sulfanylidene]cyanamide (A2), identified as diastereomer group A (known from WO 2010/074747, WO 2010/074751), [(R)-methyl(oxido){(1S)-1-[6-(trifluoromethyl)pyridin-3-yl]ethyl}-$\lambda^4$-sulfanylidene]cyanamide (B1) and [(S)-methyl (oxido){(1R)-1-[6-(trifluoromethyl)pyridin-3-yl]ethyl}-$\lambda^4$-sulfanylidene]cyanamide (B2), identified as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-{2-fluoro-4-methyl-5-[(2,2,2-trifluoroethyl)sulfinyl]phenyl}-3-(trifluoromethyl)-1H-1,2,4-triazol-5-amine (known from WO 2006/043635), [(3S,4aR,12R,12aS, 12bS)-3-[(cyclopropylcarbonyl)oxy]-6,12-dihydroxy-4, 12b-dimethyl-11-oxo-9-(pyridin-3-yl)-1,3,4,4a,5,6,6a,12, 12a,12b-decahydro-2H,11H-benzo[f]pyrano[4,3-b]chromen-4-yl]methyl cyclopropanecarboxylate (known from WO 2008/066153), 2-cyano-3-(difluoromethoxy)-N, N-dimethylbenzenesulfonamide (known from WO 2006/056433), 2-cyano-3-(difluoromethoxy)-N-methylbenzenesulfonamide (known from WO 2006/100288), 2-cyano-3-(difluoromethoxy)-N-ethylbenzenesulfonamide (known from WO 2005/035486), 4-(difluoromethoxy)-N-ethyl-N-methyl-1,2-benzothiazol-3-amine 1,1-dioxide (known from WO 2007/057407), N-[1-(2,3-dimethylphenyl)-2-(3,5-dimethylphenyl)ethyl]-4,5-dihydro-1,3-thiazol-2-amine (known from WO 2008/104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO 2003/106457), 3-(2,5-dimethylphenyl)-4-hydroxy-8-methoxy-1, 8-diazaspiro[4.5]dec-3-en-2-one (known from WO 2009/049851), 3-(2,5-dimethylphenyl)-8-methoxy-2-oxo-1,8- diazaspiro[4.5]dec-3-en-4-yl ethyl carbonate (known from WO 2009/049851), 4-(but-2-yn-1-yloxy)-6-(3,5-dimethylpiperidin-1-yl)-5-fluoropyrimidine (known from WO 2004/099160), (2,2,3,3,4,4,5,5-octafluoropentyl)(3,3,3-trifluoropropyl)malononitrile (known from WO 2005/063094), (2,2,3,3,4,4,5,5-octafluoropentyl)(3,3,4,4,4-pentafluorobutyl) malononitrile (known from WO 2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO 2007/040280), 2-ethyl-7-methoxy-3-methyl-6-[(2,2,3,3-tetrafluoro-2,3-dihydro-1,4-benzodioxin-6-yl)oxy]quinolin-4-yl methyl carbonate (known from JP2008/110953), 2-ethyl-7-methoxy-3-methyl-6-[(2,2,3,3-tetrafluoro-2,3-dihydro-1,4-benzodioxin-6-yl)oxy]quinolin-4-yl acetate (known from JP2008/110953), PF1364 (CAS Reg. No. 1204776-60-2) (known from JP 2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO 2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO 2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO 2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO 2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO 2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO 2005/085216), methyl 2-[2-({[3-bromo-1-(3-chloropyridin-2-yl)-1H-pyrazol-5-yl]carbonyl}amino)-5-cyano-3-methyl benzoyl]-2-methylhydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-1,2-diethyl hydrazinecarboxylate (known from WO 2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO 2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO 2007/101369), 2-{6-[2-(5-fluoropyridin-3-yl)-1,3-thiazol-5-yl]pyridin-2-yl}pyrimidine (known from WO 2010/006713), 2-{6-[2-(pyridin-3-yl)-1,3-thiazol-5-yl]pyridin-2-yl}pyrimidine (known from WO 2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO 2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO 2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO 2010/069502), N-[2-(tert-butylcarbamoyl)-4-cyano-6-methyl phenyl]-1-(3-chloropyridin-2-yl)-3-{[5-(trifluoromethyl)-2H-tetrazol-2-yl]methyl}-1H-pyrazole-5-carboxamide (known from WO 2010/069502), and (1E)-N-[(6-chloropyridin-3-yl)methyl]-N'-cyano-N-(2,2-difluoroethyl) ethanimideamide (known from WO 2008/009360).

Examples of herbicides include:

Usable combination partners for the inventive compounds in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 15th edition, The British Crop Protection Council and the Royal Soc. of Chemistry, 2006 and literature cited therein. Examples of known herbicides or plant growth regulators which can be combined with the inventive compounds include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. One administration form or else, in some cases, more than one administration form is mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminocyclopyrachlor-potassium, aminocyclopyrachlor-methyl, aminopyralid, amitrole, ammonium sulfamate, ancymidol, anilofos, asulam, atrazine, aviglycine, azafenidin, azimsulfuron, aziprotryne, beflubutamid, benazolin, benazolinethyl, bencarbazone, benfluralin, benfuresate, bensulide, bensulfuron, bensulfuron-methyl, bentazone, benzfendizone, benzobicyclon, benzofenap, benzofluor, benzoylprop, benzyladenine, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbaryl, carbetamide, carfentrazone, carfentrazone-ethyl, carvone, chlorocholine chloride, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, 4-chlorophenoxyacetic acid, chlorophthalim, chlorpropham, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cloxyfonac, cumyluron, cyanamide, cyanazine, cyclanilide, cycloate, cyclosulfamuron, cycloxydim, cycluron, cyhalofop, cyhalofop-butyl, cyperquat, cyprazine, cyprazole, cytokinine, 2,4-D, 2,4-DB, daimuron/dymron, dalapon, daminozide, dazomet, n-decanol, desmedipham, desmetryn, detosyl-pyrazolate (DTP), diallate, diaminozide, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, diisopropylnaphthalene, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethyl naphthylacetate, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. 0-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxy-ethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, iofensulfuron, iofensulfuron-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazin-3-amine, MT-5950, i.e. N-[3-chloro-4-(1-methylethyl)phenyl]-2-methylpentanamide, NGGC-011, 1-naphthylacetic acid (NAA), naphthylacetamide (NAAm), 2-naphthoxyacetic acid, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitroguaiacolate, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, tribufos, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

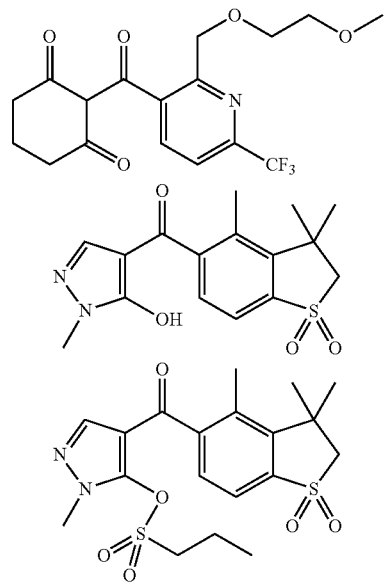

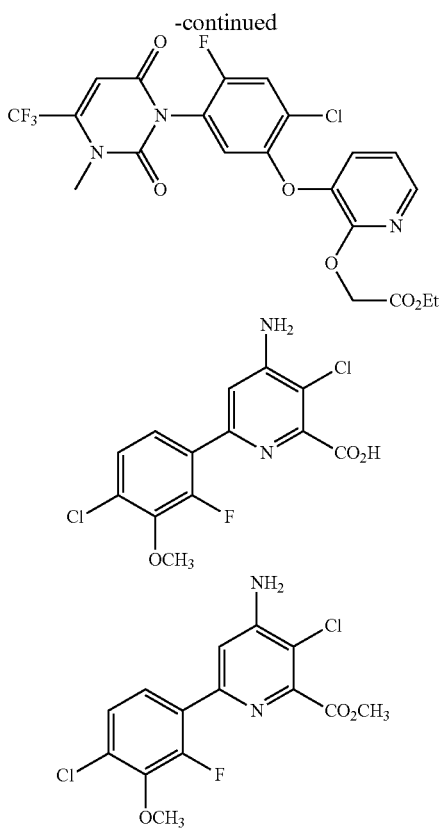

Examples of plant growth regulators further include natural plant hormones such as abscissic acid, jasmonic acid, salicylic acid and their esters, kinetin and brassinosteroids.

Examples of plant nutrients include conventional inorganic or organic fertilizers for providing plants with macronutrients and/or micronutrients.

Examples of repellents include diethyltolylamide, ethylhexanediol and butopyronoxyl.

Preferred active agrochemical ingredients are butenolides, neonicotinoids, triazoles and strobilurins, especially flupyradifurone, imidacloprid, thiacloprid, cyproconazole, epoxiconazole, metconazole, propiconazole, tebuconazole, and also azoxystrobin, fluoxastrobin, kresoxim-methyl, metominostrobin, picoxystrobin, pyraclostrobin and trifloxystrobin. Likewise preferred are all systemic leaf-applied or post-emergence herbicides and safeners, especially amidosulfuron, bromoxynil, cyprosulfamide, 2,4-D, glufosinate, glyphosate, iodosulfuron-methyl, isoxadifen-ethyl, mefenpyr, mesosulfuron, mesotrione, metamitron, phenmedipham, sulcotrione, tembotrione and thiencarbazone-methyl.

The present invention further relates to formulations and use forms prepared therefrom as crop protection compositions and/or pesticides, for example drench, drip and spray liquors, comprising at least one of the inventive active ingredients. The use forms optionally comprise further crop protection agents and/or pesticides and/or action-improving adjuvants, such as penetrants, e.g. vegetable oils, for example rapeseed oil, sunflower oil, mineral oils, for example paraffin oils, alkyl esters of vegetable fatty acids, for example rapeseed oil methyl ester or soybean oil methyl ester, or alkanol alkoxylates, and/or spreaders, for example alkylsiloxanes, and/or salts, for example organic or inorganic ammonium or phosphonium salts, for example ammonium sulfate or diammonium hydrogenphosphate, and/or retention promoters, for example dioctyl sulfosuccinate or hydroxypropyl guar polymers, and/or humectants, for example glycerol, and/or fertilizers, for example ammonium-, potassium- or phosphorus-containing fertilizers.

Examples of conventional formulations are water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible formulation types are described, for example, by Crop Life International and in Pesticide Specifications, Manual on development and use of FAO and WHO specifications for pesticides, FAO Plant Production and Protection Papers-173, prepared by the FAO/WHO Joint Meeting on Pesticide Specifications, 2004, ISBN: 9251048576. The formulations optionally comprise, as well as one or more inventive active ingredients, further active agrochemical ingredients.

These are preferably formulations or use forms which comprise auxiliaries, for example extenders, solvents, spontaneity promoters, carriers, emulsifiers, dispersants, antifreezes, biocides, thickeners and/or further auxiliaries, for example adjuvants. An adjuvant in this context is a component which enhances the biological effect of the formulation, without the component itself having any biological effect. Examples of adjuvants are agents which promote retention, spreading, adhesion to the leaf surface or penetration.

These formulations are produced in a known manner, for example by mixing the active ingredients with auxiliaries, for example extenders, solvents and/or solid carriers and/or further auxiliaries, for example surfactants. The formulations are produced either in suitable facilities or else before or during application.

The auxiliaries used may be substances suitable for imparting special properties, such as certain physical, technical and/or biological properties, to the formulation of the active ingredient, or to the use forms prepared from these formulations (for example ready-to-use crop protection compositions such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and the ethers and esters thereof, ketones, for example acetone, methyl ethyl ketone, methyl isobutyl ketone or cyclohexanone, strongly polar solvents such as dimethyl sulfoxide, and water.

In principle, it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, maize cobs and tobacco stalks.

Liquefied gaseous extenders or solvents can also be used. Particularly suitable extenders or carriers are those which are gaseous at standard temperature and under standard pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, include salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkylsulfates, arylsulfonates, protein hydrolysates, lignosulfite waste liquors and methylcellulose. The presence of a surfactant is advantageous when one of the active ingredients and/or one of the inert carriers is insoluble in water and when application is effected in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam formers or antifoams may also be present.

In addition, the formulations and the use forms derived therefrom may also comprise, as additional auxiliaries, stickers such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the active ingredients can be combined with any solid or liquid additive which is commonly used for formulation purposes.

Useful retention promoters include all those substances which reduce the dynamic surface tension, for example dioctyl sulfosuccinate, or increase the viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and thereby increase the mobility of active ingredients in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations contain preferably between 0.00000001% and 98% by weight of active ingredient or more preferably between 0.01% and 95% by weight of active ingredient, more preferably between 0.5% and 90% by weight of active ingredient, based on the weight of the formulation.

The active ingredient content of the use forms (crop protection compositions) prepared from the formulations can vary within wide limits. The active ingredient concentration of the use forms may typically be between 0.00000001% and 95% by weight of active ingredient, preferably between 0.00001% and 1% by weight, based on the weight of the use form. Application is accomplished in a customary manner appropriate for the use forms.

The content of the individual components in the inventive formulations can be varied within a relatively wide range.

The inventive formulations are produced, for example, by mixing the components with one another in the particular ratios desired. If the active agrochemical ingredient is a solid substance, it is generally used either in finely ground form or in the form of a solution or suspension in an organic solvent or water. If the active agrochemical ingredient is liquid, there is frequently no need to use an organic solvent. It is also possible to use a solid active agrochemical ingredient in the form of a melt.

The temperatures can be varied within a particular range in the course of performance of the process. In general, working temperatures are between 0° C. and 80° C., preferably between 10° C. and 60° C.

In the performance of the process according to the invention, the procedure is generally to mix the etherified lactate esters of the formula (I) with one or more active ingredients and optionally with additives. The sequence in which the components are mixed with one another is arbitrary.

Useful equipment for performance of the process according to the invention is customary equipment which is used for production of agrochemical formulations.

Examples of administration forms include all the processes known as commonly used to the person skilled in the art: spraying, dipping, misting and a number of specific processes for direct treatment below or above ground of whole plants or parts (seed, root, stolons, stem, trunk, leaf), for example trunk injection in the case of trees or stem bandages in the case of perennial plants, and a number of specific indirect application processes.

The term "harmful organisms" encompasses all forms of organisms which cause economic and/or health damage in the particular field of use. Preference is given to organisms harmful to vegetables and animals, and to organisms which cause diseases, particular preference being given to terrestrial and aquatic weed grasses and broad-leaved weeds, algae, mosses, insects, mites, nematodes, rodents, fungi, bacteria and viruses.

The respective area- and/or object-based application rate of the crop protection compositions of a wide variety of different formulation types for control of the harmful organisms mentioned here varies very greatly. In general, the application media known to the person skilled in the art to be commonly used for the respective field of use are used in the customary amounts for this purpose, for example several hundred liters of water per hectare in the case of standard spraying processes through a few liters of oil per hectare in the case of 'ultra low volume' aircraft application down to a few milliliters of a physiological solution in the case of injection processes. The concentrations of the inventive crop protection compositions in the particular application media therefore vary within a wide range and are dependent on the respective field of use. In general, concentrations known to the person skilled in the art to be commonly used for the respective field of use are used. Preferred concentrations are from 0.01% by weight to 99% by weight, more preferably from 0.1% by weight to 90% by weight.

The inventive crop protection compositions can be deployed, for example, in the formulation forms customary for liquid preparations, either as such or after prior dilution with water, i.e., for example, as emulsions, suspensions or solutions. Application is effected by customary methods, i.e., for example by spraying, pouring or injecting.

The application rate of the inventive crop protection compositions can be varied within a relatively wide range. It is guided by the active agrochemical ingredients in question and by the content thereof in the crop protection compositions.

According to the invention, it is possible to treat all plants and plant parts. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. Plant parts also include harvested material and vegetative and generative propagation material, for example cuttings, tubers, rhizomes, slips and seeds.

As already mentioned above, it is possible to treat all plants and parts thereof in accordance with the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. More preferably, plants of the plant cultivars which are respectively commercially available or are in use are treated in accordance with the invention. Plant cultivars are understood to mean plants which have new properties ("traits") and have been obtained by conventional breeding, by mutagenesis or by recombinant DNA techniques. They may be cultivars, varieties, biotypes or genotypes.

The preferred transgenic plants or plant cultivars (those obtained by genetic engineering) which are to be treated in accordance with the invention include all plants which, through the genetic modification, received genetic material which imparts particular advantageous useful traits to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, longer storage life and/or processability of the harvested products. Further and particularly emphasized examples of such properties are an improved defense of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soybeans, potatoes, sugarbeet, tomatoes, peas and other vegetable types, cotton, tobacco, oilseed rape, and also fruit plants (with the fruits of apples, pears, citrus fruits and grapes), particular emphasis being given to maize, soybeans, potatoes, cotton, tobacco and oilseed rape. Traits that are particularly emphasized are improved defense of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defense of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal ingredients, for example imidazolinones, sulfonylureas, glyphosate or phosphinothricin (for example the "PAT" gene). The genes which impart the desired traits in question can also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soybean varieties which are sold under the trade names Roundup Ready® (tolerance against glyphosate, for example maize, cotton, soybeans), Liberty Link® (tolerance against phosphinothricin, for example oilseed rape), IMI® (tolerance against imidazolinones) and STS® (tolerance against sulfonylureas, for example maize). Herbicide-resistant plants (plants bred in a conventional manner for herbicide tolerance) also include the varieties sold under the Clearfield® name (for example maize). Of course, these statements also apply to plant cultivars which have these genetic traits or genetic traits which are still to be developed and will be developed and/or marketed in the future.

Preferred plants are those from the group of the useful plants, ornamental plants, turfgrass types, commonly used trees which are employed as ornamentals in public and domestic areas, and forestry trees. Forestry trees include trees for the production of timber, cellulose, paper and products made from parts of the trees.

The term useful plants as used here refers to crop plants which are employed as plants for obtaining foods, animal feeds, fuels or for industrial purposes.

The useful plants which can be treated in accordance with the invention include, for example, the following plant species: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fiber plants, for example cotton, flax, hemp and jute; citrus fruit, for example, oranges, lemons, grapefruit and tangerines; vegetables, for example spinach, lettuce, asparagus, cabbage species, carrots, onions, tomatoes, potatoes and bell peppers; *Lauraceae*, for example avocado, *Cinnamomum*, camphor, or also plants such as tobacco, nuts, coffee, aubergine, sugarcane, tea, pepper, grapevines, hops, bananas, latex plants and ornamentals, for example flowers, shrubs, deciduous trees and coniferous trees. This enumeration does not constitute a limitation.

The following plants are considered to be particularly suitable target crops for the application of the process according to the invention: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potatoes and apples.

The plants treated in accordance with the invention are, where the use of herbicides is concerned, all kinds of weeds. With regard to the protection of crop plants through application of, for example, fungicides and insecticides, preference is given to application in economically important crops, for example including transgenic crops, of useful plants and ornamentals, for example of cereals such as wheat, barley, rye, oats, millet/sorghum, rice, manioc and maize, or else crops of sugar beet, cotton, soybean, oilseed rape, potato, tomato, peas and other vegetables.

The invention is illustrated in detail by the examples but is not restricted thereto.

EXAMPLES

Preparation of Inventive Etherified Lactate Esters

Raw Materials Used:

Catalyst for the alkylene oxide addition reaction (DMC-catalyst): Double metal cyanide catalyst, containing zinc hexacyanocobaltate, tert-butanol, and polypropylene glycol with a number-average molecular weight of 1000 g/mol; described in WO-A 01/80994, example 6.

2-Ethylhexyl lactate, acquired from the company Galactic Lauryl lactate (PURASOLV LL®), acquired from the company PURAC IRGANOX® 1076: octadecyl 3-(3,5-di-tert-butyl-4-hydroxy-phenyl)propionate. (BASF SE)

Preparation of the Inventive Etherified Lactate Esters Based on Ethylhexyl Lactate A) 2-ethylhexyl lactate 2PO/2EO A 2 l laboratory autoclave was charged at 100° C. under a nitrogen atmosphere with 160.0 g (0.792 mol) of 2-ethylhexyl lactate and 0.067 g of DMC catalyst. After 5-fold nitrogen/vacuum exchange between 0.1 and 3.0 bar (absolute), the initial charge was heated to 130° C. Then, at this temperature, with stirring, 91.88 g (1.584 mol) of PO were metered into the reactor over the course of 10 minutes, the pressure in the reactor rising from 0.21 bar (absolute) to 0.54 bar (absolute). After a subsequent reaction time of 25 minutes, the reactor pressure was first adjusted with nitrogen to 2.15 bar (absolute), and subsequently, with stirring at 130° C. 69.68 g (1.584 mol) of EO were metered into the reactor over the course of 10 minutes, the pressure rising from 2.15 bar (absolute) to 2.37 bar (absolute). After a subsequent reaction time of 45 minutes, volatile fractions were removed by heating under reduced pressure at 90° C. for 30 minutes, and the reaction mixture was then cooled to room temperature. The product, lastly, was admixed with 161 mg of IRGANOX® 1076.

The products with compositions of "2-ethylhexyl lactate 2PO/5EO" and "2-ethylhexyl lactate 2PO/10EO" from table 1 were prepared analogously.

B) 2-ethylhexyl lactate 2EO

A 2 l laboratory autoclave was charged at 100° C. under a nitrogen atmosphere with 160.0 g (0.792 mol) of 2-ethylhexyl lactate and 0.007 g of DMC catalyst. After 5-fold nitrogen/vacuum exchange between 0.1 and 3.0 bar (absolute), the initial charge was heated to 130° C., and the reactor pressure was then adjusted with nitrogen to 2.19 bar (absolute). Subsequently with stirring at 130° C., 69.68 g (1.584 mol) of EO were metered into the reactor over the course of 30 minutes, the pressure in the reactor rising from 2.19 bar (absolute) to 2.61 bar (absolute). After a subsequent reaction time of 60 minutes, volatile fractions were removed by heating under reduced pressure at 90° C. for 30 minutes, and the reaction mixture was then cooled to room temperature. The product, lastly, was admixed with 115 mg of IRGANOX® 1076.

The products with compositions of "2-ethylhexyl lactate 5EO", and "2-ethylhexyl lactate 10EO", and, "2-ethylhexyl lactate 15EO" from table 1 were prepared analogously.

Preparation of the Inventive Etherified Lactate Esters Based on Lauryl Lactate

C) Lauryl Lactate 5EO/2PO

A 2 l laboratory autoclave was charged under a nitrogen atmosphere with 50 g of PURASOLV LL®. Following addition of 2 mg of 85% strength phosphoric acid, the contents of the reactor were stirred at room temperature for 20 minutes (200 rpm, propeller stirrer). Following addition of 12 mg of DMC catalyst, the contents of the autoclave were heated to 130° C. and subjected to stripping for 30 minutes at this temperature with stirring at 800 rpm under reduced pressure, with an absolute pressure of 100 to 120

Mbar, with introduction of 50 ml of nitrogen per minute via a distributor ring lying beneath the level of the liquid. This distributor ring was then used for metered introduction, likewise at 130° C. with stirring at 800 rpm, of a total of 39.4 g of ethylene oxide over a period of 58 minutes. Following a subsequent reaction time of 17 minutes, 20.8 g of propylene oxide were metered in over a period of 30 minutes at 130° C. with stirring at 800 rpm. After a subsequent reaction time of 22 minutes, the product was heated to remove volatiles for 30 minutes under an absolute pressure of 1 mbar, and then cooled to 80° C. The autoclave was let down with nitrogen to about 1 bar. 50 g of product were discharged from the autoclave and admixed with 30 mg of IRGANOX® 1076.

D) Lauryl Lactate 5EO/5PO

The remaining autoclave content of the product from example C) was heated to 130° C. with stirring (800 rpm), after which a further 17.1 g of propylene oxide were metered in over a period of 34 minutes. After a subsequent reaction time of 30 minutes, the product was heated to remove volatiles for a further 30 minutes under an absolute pressure of 1 mbar. Thereafter the autoclave was let down with nitrogen to about 1 bar, and cooling to 80° C. took place. The product was discharged and admixed with 47 mg of IRGANOX® 1076.

E) Laurel Lactate 8EO/2PO

A 2 l laboratory autoclave was charged under a nitrogen atmosphere with 152.0 g of PURASOLV LL®. Following addition of 11 mg of 85% strength phosphoric acid, the contents of the reactor was stirred at room temperature for 20 minutes (200 rpm, propeller stirrer). Following addition of 56 mg of DMC catalyst, the contents of the autoclave were heated to 130° C. and subjected to stripping for 30 minutes at this temperature with stirring at 800 rpm under reduced pressure, with an absolute pressure of 100 to 120 Mbar, with introduction of 50 ml of nitrogen per minute via a distributor ring lying beneath the level of the liquid. This distributor ring was then used for metered introduction, likewise at 130° C. with stirring at 800 rpm, of a total of 191.7 g of ethylene oxide over a period of 4.03 hours. Following a subsequent reaction time of 10 minutes, 63.2 g of propylene oxide were metered in over a period of 2.0 hours at 130° C. with stirring at 800 rpm. After a subsequent reaction time of 30 minutes, the product was heated to remove volatiles for 30 minutes under an absolute pressure of 1 mbar, and then cooled to 80° C. The autoclave was let down with nitrogen to about 1 bar. 76.9 g of product were discharged from the autoclave and admixed with 41 mg of IRGANOX® 1076.

F) Laurel Lactate 8EO/5PO

The remaining autoclave content of the product from example E) was heated to 130° C. with stirring (800 rpm), after which a further 77.2 g of propylene oxide were metered in over a period of 1.02 hours. After a subsequent reaction time of 26 minutes, the product was heated to remove volatiles for a further 30 minutes under an absolute pressure of 1 mbar. Thereafter the autoclave was let down with nitrogen to about 1 bar, and cooling to 80° C. took place. The product was discharged and admixed with 204 mg of IRGANOX® 1076.

Use

The etherified lactate esters possess very good properties as surfactants. Surfactants find use in sectors including crop protection, as wetters and stickers and also as emulsifiers. Their suitability as wetters is characterized, for example, by the static surface tension; their suitability as stickers by the dynamic surface tension (see Adamson A W 1990. Physical Chemistry of Surfaces. London, Wiley/Berger P D & Berger C H, 1993. Effect of Surfactant Type and Order of Addition on Droplet Size and Dynamic Interfacial Properties. Pesticide formulations and application systems, 13th Vol., Berger, P D, Debisetty, B N, Hall, F R, Eds., American Society for testing and Materials/Knowles, D A 1998. Chemistry and Technology of Agrochemical Formulations, Kluwer Academic Publishers, Dordrecht).

1) Static Surface Tension in Aqueous Systems

The surface tension value achievable in equilibrium was determined via the Pending Drop Method using a Goniometer (DSA10 Goniometer, Krüss), The table shows the results of the measurements on the etherified lactate esters at 0.3 and 3 g/l at room temperature (20° C.) in comparison to literature values for two frequently used surfactants.

TABLE 1

| Test substance | Static surface tension (mN/m) | |
|---|---|---|
| | 0.3 g/l | 3 g/l |
| Lauryl lactate 5EO/2PO | 31.63 | 31.34 |
| Lauryl lactate 5EO/5PO | 31.65 | 30.14 |
| Lauryl lactate 8EO/2PO | 30.76 | 30.71 |
| Lauryl lactate 8EO/5PO | 31.38 | 31.51 |
| 2-Ethylhexyl lactate 2PO/2EO | 40.40 | 29.47 |
| 2-Ethylhexyl lactate 2PO/5EO | 43.35 | 28.48 |
| 2-Ethylhexyl lactate 2PO/10EO | 47.43 | 36.0 |
| 2-Ethylhexyl lactate 2EO | 45.34 | 28.19 |
| 2-Ethylhexyl lactate 5EO | 48.65 | 32.61 |
| 2-Ethylhexyl lactate 10EO | 52.99 | 35.18 |
| 2-Ethylhexyl lactate 15EO | 54.33 | 42.23 |
| Comparative (commercial) | | |
| Frigate* (tallowamine ethoxylate) | — | 39.6 |
| Tanemul HOT** (ethylhexyl alkoxylate) | 35.2 | 29.7 |

*ISK Biosciences, Diegem (Belgium),
**Tanatex, Leverkusen (Germany) Here, for example, lauryl lactate 5EO/2PO means that for this etherified lactate ester, in the notation of formula (I), R is lauryl and R1 is —(—AO)$_m$—R', where AO is a mixture of ethylene oxide (EO) radicals and propylene oxide (PO) radicals, the first EO fraction bonding to the lactate ester group, and the subsequent PO fraction bonding to the EO radicals, m is 5 + 2 = 7, and R' is hydrogen.

2) Dynamic Surface Tension (Interfacial Activity)

The dynamic surface tension was determined via the bubble pressure method (BP2100, tensiometer, Krüss). With a time span relevant for the spray application of agrochemicals in aqueous dilution (referred to as the surface age in the bubble pressure method) of 200 milliseconds, the value of the dynamic surface tension in [mN/m] correlates with the adherence on difficult-to-wet plants such as barley (cereal). A value of 50 mN/m (at 20-21° C.) produces, relative to water (72.8 mN/m), an improvement in the adherence from "zero adherence" to about 50% (Baur P, Pontzen R 2007. Basic features of plant surface wettability and deposit formation and the impact of adjuvants. In: R E Gaskin ed. Proceeding of the 8th International Symposium on Adjuvants for Agrochemicals. Publisher: International Society for Agrochemical Adjuvants (ISAA), Columbus, Ohio, USA). Table 2 shows that this value is attained by many etherified lactate esters even at the low test concentration in water, and that all of them fall below this value clearly at 3 g/l. The etherified lactate esters are therefore outstandingly suitable for promoting the accommodation of agrochemicals by cereals (with maize, rice, millet), banana, cabbage/oil seed rape, soybean, and other difficult-to-wet crop plants and weed plants. The positive wetting and sticking effects also apply, of course, for other organisms and artificial surfaces and/or technical applications, for the purpose, for instance, of achieving thin coatings on, or cleaning, surfaces.

TABLE 2

| Test substance | Dynamic surface tension (mN/m) | |
|---|---|---|
| | 0.3 g/l | 3 g/l |
| Lauryl lactate 5EO/2PO | 51.9 | 37.4 |
| Lauryl lactate 5EO/5PO | 52.7 | 36.5 |
| Lauryl lactate 8EO/2PO | 54.3 | 37.7 |
| Lauryl lactate 8EO/5PO | 50.9 | 36.2 |
| 2-Ethylhexyl lactate 2PO/2EO | 47.8 | 30.7 |
| 2-Ethylhexyl lactate 2PO/5EO | 50.7 | 29.6 |
| 2-Ethylhexyl lactate 2PO/10EO | 54.2 | 37.4 |
| 2-Ethylhexyl lactate 2EO | 50.9 | 26.8 |
| 2-Ethylhexyl lactate 5EO | 54.4 | 35.3 |
| 2-Ethylhexyl lactate 10EO | 56.6 | 46.6 |
| 2-Ethylhexyl lactate 15EO | 58.6 | 48.1 |
| Comparative (commercial) | | |
| Frigate* (tallowamine ethoxylate) | — | 50.9 |
| Tanemul HOT** (ethylhexyl alkoxylate) | 44.3 | 31.5 |

*ISK Biosciences, Diegem (Belgium),
**Tanatex, Leverkusen (Germany)

3) Promotion of Penetration of Exemplarily Selected Active Ingredients

Surfactants may also promote the uptake of (active) ingredients through membranes such as skin, films, or the plant cuticle. In the form of what is called "finite dose" application, it is known, for the single administration or application of a solution, cream, gel, etc. to a membrane, that the uptake of active ingredient can be influenced, even after wetting has taken place, by certain adjuvants such as surfactants. This effect is independent of the surfactant activity, is often highly concentration-dependent, and to a very large extent occurs following volatilization of water and any solvents present, as a consequence of interaction with, for example, active ingredient, membrane, and environmental factors. For various surfactants it is observed, following addition onto active ingredient preparations, that the penetration of a particular active ingredient is massively promoted by some surfactants, while others are completely inactive (Cronfeld, P, Lader, K. Baur, P. (2001). Classification of Adjuvants and Adjuvant Blends by Effects on Cuticular Penetration, Pesticide Formulations and Application Systems: Twentieth Volume, ASTM STP 1400, A. K. Viets, R. S. Tann, J. C. Mueninghoff, Edsl, American Society for Testing and Materials, West Conshohocken, Pa. 2001).

The potential, independent of the surfactant activity, to promote the leaf uptake of active agrochemical ingredients was determined in membrane penetration experiments with leaf cuticles of apple. The principle of the method has been published (e.g., WO-A-2005/194844), and only the specifics and methodological deviations are explained below. The leaf cuticles were isolated enzymatically in the manner described from apple leaves from field trees in a commercial pome fruit orchard at Kriftel, to the west of Frankfurt, in 2010. After they had been dried in air, the cuticles were installed into stainless steel diffusion cells. After application to the original top leaf face and evaporation of the test fluid, i.e., of the aqueous preparations of the active ingredients without or with the etherified lactate esters, the diffusion cells were transferred to thermostated blocks and were filled with aqueous liquid. The water used to prepare the aqueous test liquids was local tap water (known composition). At regular intervals, samples were taken and the penetrated fraction of active ingredient was determined, depending on the test system, either by HPLC or by scintillation measurement. In the system with radiolabeled active ingredient (thiacloprid and fluoxastrobin), the aqueous liquid was a phospholipid suspension and the entire quantity was replaced. In the case of the HPLC variant (tebuconazole SC430), only an aliquot was removed. During the experiment, the temperature in the system (block, diffusion cells, liquids, etc.) and the atmospheric humidity over the spray coating on the cuticle was precisely known and monitored. In each of the experiments, the relative humidity was kept consistently at a constant 60%, but the temperature was increased after one day by 10° C., specifically from 20° C. to 30° C. for thiacloprid and tebuconazole, and from 15° C. to 25° C. for fluoxastrobin. Depending on variant (active ingredient x, etherified lactate ester), 7-8 repetitions were set up.

Set out by way of example below is the promotion of uptake by the etherified lactate esters on tank-mix addition to 1) a solution of the insecticide thiacloprid with 0.5 g/l and 3 g/l etherified lactate ester 2) to a suspension concentrate of the fungicide tebuconazole with 0.5 g/l and 2 g/l etherified lactate ester 3) a solution of fungicide fluoxastrobin with 0.5 g/l and 2 g/l etherified lactate ester in each case in comparison to the systems without addition of the etherified lactate esters.

TABLE 3

| | Mean penetration of thiacloprid* in % (n = 4-8) | | | |
|---|---|---|---|---|
| | 0.5 g/l | | 3 g/l | |
| Etherified lactate ester | 24 h** | 48 h*** | 24 h** | 48 h*** |
| Thiacloprid in solution in acetone/water without etherified lactate ester | <3 | <5 | <3 | <5 |
| Lauryl lactate 5EO/2PO | 13.6 | 17.4 | 63.9 | 74.5 |
| Lauryl lactate 5EO/5PO | 18.6 | 24.0 | 67.4 | 76.3 |
| Lauryl lactate 8EO/2PO | 14.5 | 18.8 | 73.3 | 80.4 |
| Lauryl lactate 8EO/5PO | 20.5 | 27.3 | 72.0 | 82.9 |
| 2-Ethylhexyl lactate 2PO/2EO | 11.5 | 15.1 | 20.3 | 23.4 |
| 2-Ethylhexyl lactate 2PO/5EO | 10.2 | 12.1 | 43.2 | 49.2 |
| 2-Ethylhexyl lactate 2PO/10EO | 8.1 | 10.0 | 36.9 | 47.2 |
| 2-Ethylhexyl lactate 2EO | 5.6 | 6.5 | 35.5 | 43.0 |
| 2-Ethylhexyl lactate 5EO | 12.1 | 14.1 | 31.4 | 39.9 |
| 2-Ethylhexyl lactate 10EO | 11.0 | 12.4 | 39.6 | 46.2 |
| 2-Ethylhexyl lactate 15EO | 10.5 | 14.0 | 29.9 | 41.9 |

*0.2 g/l thiacloprid;
**20° C./60% relative humidity (RH);
***30° C./60% RH

TABLE 4

| | Mean penetration of tevuconazole* in % (n = 4-8) | | | |
|---|---|---|---|---|
| | 0.5 g/l | | 2 g/l | |
| Etherified lactate ester | 24 h** | 48 h*** | 24 h** | 48 h*** |
| Tebuconazole SC 430 without etherified lactate ester | 2.2 | 20.5 | 2.2 | 20.5 |
| Lauryl lactate 5EO/2PO | 27.6 | 75.1 | 57.1 | 68.3 |
| Lauryl lactate 5EO/5PO | 36.9 | 36.9 | 59.0 | 74.0 |
| Lauryl lactate 8EO/2PO | 25.4 | 62.9 | 62.9 | 73.3 |
| Lauryl lactate 8EO/5PO | 45.6 | 75.9 | 41.0 | 56.9 |
| 2-Ethylhexyl lactate 2PO/2EO | 23.2 | 58.1 | 27.0 | 36.5 |
| 2-Ethylhexyl lactate 2PO/5EO | 31.7 | 74.8 | 53.9 | 71.1 |
| 2-Ethylhexyl lactate 2PO/10EO | — | — | 52.2 | 79.3 |
| 2-Ethylhexyl lactate 2EO | — | — | 42.1 | 42.1 |
| 2-Ethylhexyl lactate 5EO | — | — | 45.0 | 63.8 |
| 2-Ethylhexyl lactate 10EO | — | — | 42.3 | 78.1 |
| 2-Ethylhexyl lactate 15EO | — | — | 30.5 | 53.6 |

*0.5 g/l tebuconazole;
**20° C./60% RH;
***30° C./60% RH

TABLE 5

| | Mean penetration of fluoxastrobin* in % (n = 4-8) | | | |
|---|---|---|---|---|
| | 0.5 g/l | | 2 g/l | |
| Etherified lactate ester | 24 h** | 48 h*** | 24 h** | 48 h*** |
| Fluoxastrobin in solution in acetone/water without etherified lactate ester | 2.6 | 6.9 | 2.6 | 6.9 |
| Commercial fluoxastrobin EC formulation 3 g/l | 1.8 | 7.3 | 1.8 | 7.3 |
| Lauryl lactate 5EO/2PO | 3.3 | 7.5 | 12.7 | 25.6 |
| Lauryl lactate 5EO/5PO | 4.7 | 10.0 | 12.2 | 23.1 |
| Lauryl lactate 8EO/2PO | 4.0 | 7.8 | 11.5 | 20.4 |
| Lauryl lactate 8EO/5PO | 3.9 | 9.6 | 6.8 | 19.8 |
| 2-Ethylhexyl lactate 2PO/2EO | 12.1 | 18.6 | 16.1 | 26.0 |
| 2-Ethylhexyl lactate 2PO/5EO | 9.9 | 16.2 | 14.4 | 24.2 |
| 2-Ethylhexyl lactate 2PO/10EO | 8.9 | 17.5 | 13.1 | 22.1 |
| 2-Ethylhexyl lactate 2EO | 10.6 | 35.2 | 11.4 | 18.9 |
| 2-Ethylhexyl lactate 5EO | 8.7 | 13.9 | 13.0 | 21.4 |
| 2-Ethylhexyl lactate 10EO | 9.7 | 15.9 | 16.8 | 26.9 |
| 2-Ethylhexyl lactate 15EO | 9.5 | 14.1 | 13.4 | 25.8 |

*0.3 g/l fluoxastrobin;
**15° C./60% RH;
***25° C./60% RH;

Tables 3 to 5 show the outstanding suitability of the etherified lactate esters of the invention, as a function of concentration, for greatly promoting leaf penetration for a variety of active ingredients, active ingredient preparations (solutions in the case of thiacloprid and fluoxastrobin; suspension concentrate in the case of tebuconazole), and environmental factors. The relative independence from the degree of ethoxylation or alkoxylation and from the capacity to promote penetration, and the difference in interfacial activity at the same time, means that the etherified lactate esters are also components of interest for incorporation into agrochemical formulations.

4) Foam Behavior

The important properties of interface-active substances include the foam behavior, particularly in aqueous systems. Virtually all surfactants foam, and the time to collapse of the foam has to be shortened in the case of critical (highly foaming) surfactants through addition of defoamers to formulation or to aqueous use preparation. The foam behavior of certain of the substances of the invention was characterized, using aqueous solutions at a concentration of 3 g/l, by the foam test of CIPAC Method MT47. The values in the table show the percentage filling with foam in a cylinder over a period of 12 minutes. A value of 100(%), therefore, denotes maximum foam and is obtained, for example, over the entire 12-minute period with lauryl ether sulfates (such as Genapol LRO).

Using the etherified ethylhexyl lactate esters of the invention as an example, the table below shows that the foam behavior of the substances can be classed as very favorable. At the concentration of 3 g/l, which is relatively high, for example, for use in agrochemical aqueous spray mixtures, collapse of the foam is very quick. It is surprising also in the case of the ethoxylated ethylhexyl lactate esters of the invention that only the 5 EO degree of ethoxylation exhibits an initially relatively great foam behavior, whereas higher and lower degrees of ethoxylation produced virtually no foam or none. The comparative is the result with the alkoxylated ethylhexyl lactate esters (mixed EO/PO) of the invention, despite the fact that these are also stronger surfactants (see tables 1 and 2).

TABLE

| | Percentage foam volume* | | | |
|---|---|---|---|---|
| Etherified lactate ester | 10 s | 60 s | 3 min | 12 min |
| Ethylhexyl lactate 2PO/2EO | 2 | 2 | 0 | 0 |
| Ethylhexyl lactate 2PO/5EO | 25 | 10 | 10 | 10 |
| Ethylhexyl lactate 2PO/10EO | 50 | 10 | 0 | 0 |
| 2-Ethylhexyl lactate 2EO | 5 | 5 | 5 | 5 |
| 2-Ethylhexyl lactate 5EO | 50 | 40 | 20 | 10 |
| 2-Ethylhexyl lactate 10EO | 10 | 5 | 5 | 0 |
| 2-Ethylhexyl lactate 15EO | 0 | 0 | 0 | 0 |

*CIPAC MT47 foam test with CIPAC D water (342 ppm); concentration of 3 g/l

5) Crop Tolerance

At the concentrations where the significantly promoting effects on wetting and uptake of agrochemicals were found, the tolerance by crops of the etherified lactate esters (lactate ester ethoxylates) was very good.

The invention claimed is:

1. An etherified lactate ester of the formula (I)

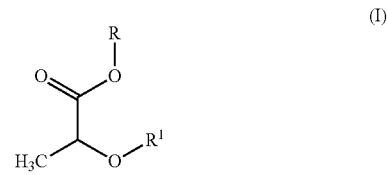

wherein

R is 2-ethylhexyl or lauryl, and $R^1$ is an alkoxylated alkyl radical of the formula -(-AO)$_m$—R', where AO is an ethylene oxide radical (EO), a propylene oxide radial (PO), a butylene oxide radical (BO), or mixtures of ethylene oxide and propylene oxide radicals or mixtures of ethylene oxide and butylene oxide radicals, and m is a number from 2 to 20, R' is hydrogen.

2. The etherified lactate ester as claimed in claim 1, wherein

R is 2-ethylhexyl, or lauryl, $R^1$ is an alkoxylated alkyl radical of the formula $-(-AO)_m-R'$, where AO is an ethylene oxide radical, a propylene oxide radical, a butylene oxide radical, or mixtures of ethylene oxide and propylene oxide radicals, and m is a number from 2 to 15, R' is hydrogen.

3. The etherified lactate ester as claimed in claim 1, wherein

R is lauryl, $R^1$ is $-(-AO)_m-R'$, where R' is hydrogen and $-(-AO)_m$ is selected from the group consisting of the following alkoxylate radicals: $-(EO)_5-(PO)_2$, $-(EO)_5-(PO)_5$, $-(EO)_8-(PO)_2$, $-(EO)_8-(PO)_5$.

4. The etherified lactate ester as claimed in claim 1, wherein

R is ethylhexyl, $R^1$ is $-(-AO)_m-R'$, where R' is hydrogen and $-(-AO)_m$ is selected from the group consisting of the following alkoxylate radicals: $-(EO)_2-(PO)_2$, $-(EO)_2-(PO)_5$, $-(EO)_2-(PO)_{10}$, $-(EO)_2$, $-(EO)_5$, $-(EO)_{10}$, $-(EO)_{15}$.

5. An etherified lactate ester of the formula (I)

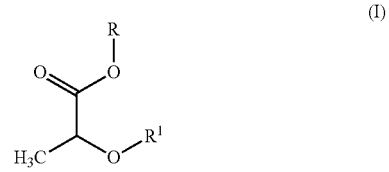

wherein

R is 2-ethylhexyl, $R^1$ is an alkoxylated alkyl radical of the formula $-(-AO)_m-R'$, where AO is an ethylene oxide radical, m is 10, and R' is hydrogen.

* * * * *